US010922943B2

(12) United States Patent
Yarlagadda et al.

(10) Patent No.: US 10,922,943 B2
(45) Date of Patent: *Feb. 16, 2021

(54) MULTI-SENSOR INPUT ANALYSIS FOR IMPROVED SAFETY

(71) Applicant: Honeywell International Inc., Morris Plains, NJ (US)

(72) Inventors: Edukondalu Yarlagadda, Lincolnshire, IL (US); Praveen Sharma, Dublin, CA (US); Thomas Negre, San Jose, CA (US); James Liu, Livermore, CA (US); Peter Hsi, Dublin, CA (US); Neal Muggleton, Stevenage (GB); Swapnil Patil, Bhiwandi (IN); Aleks Todorovic, Thomastown (AU)

(73) Assignee: HONEYWELL INTERNATIONAL INC., Charlotte, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/855,434

(22) Filed: Apr. 22, 2020

(65) Prior Publication Data
US 2020/0250952 A1    Aug. 6, 2020

Related U.S. Application Data

(63) Continuation of application No. 16/460,566, filed on Jul. 2, 2019, now Pat. No. 10,665,077, which is a (Continued)

(30) Foreign Application Priority Data

Apr. 16, 2015    (IN) ............................ 1065/DEL/2015

(51) Int. Cl.
*G08B 23/00*    (2006.01)
*G08B 21/02*    (2006.01)
(Continued)

(52) U.S. Cl.
CPC ..... *G08B 21/02* (2013.01); *G06Q 10/063114* (2013.01); *G06Q 10/063118* (2013.01);
(Continued)

(58) Field of Classification Search
CPC ............................ G08B 21/02; G08B 21/182
(Continued)

(56) References Cited

U.S. PATENT DOCUMENTS 10,665,077 B2 *  5/2020  Yarlagadda .... G06Q 10/063118
2005/0068171 A1   3/2005  Kelliher et al.
(Continued)

FOREIGN PATENT DOCUMENTS

CN    107690664 A    2/2018
EP      3284055 A1   2/2018
(Continued)

OTHER PUBLICATIONS

Annex to the communication dated Aug. 30, 2018 for EP Application No. 16720614.
(Continued)

*Primary Examiner* — Tanmay K Shah
(74) *Attorney, Agent, or Firm* — Alston & Bird LLP

(57) ABSTRACT

A method of limiting noise damage to an individual includes receiving, by an ototoxicity application stored in a non-transitory memory and executed on a processor, a first individual exposure level to a first oto-toxic condition in an area, correlating the first individual exposure level to an ototoxic effect, determining a noise level threshold based on the correlating, receiving a noise level exposure in the area, comparing the noise level threshold with the noise level exposure, and sending an alert when the noise level exposure exceeds the noise level threshold. The noise level threshold is below a standard noise level threshold.

20 Claims, 2 Drawing Sheets

Related U.S. Application Data continuation of application No. 15/564,644, filed as application No. PCT/US2016/027572 on Apr. 14, 2016, now Pat. No. 10,388,137.

(51) Int. Cl.
    *G08B 21/18*     (2006.01)
    *G06Q 10/06*     (2012.01)
    *G16H 40/67*     (2018.01)
    *G08B 21/12*     (2006.01)

(52) U.S. Cl.
    CPC ........... *G08B 21/182* (2013.01); *G16H 40/67* (2018.01); *G08B 21/12* (2013.01)

(58) Field of Classification Search
    USPC ...................................................... 340/573.1
    See application file for complete search history.

(56) References Cited

U.S. PATENT DOCUMENTS

| | | |
|---|---|---|
| 2005/0110637 A1 | 5/2005 | Rao |
| 2006/0140425 A1 | 6/2006 | Berg et al. |
| 2006/0225352 A1 | 10/2006 | Fischer et al. |
| 2007/0018836 A1 | 1/2007 | Richardson |
| 2009/0085873 A1 | 4/2009 | Betts et al. |
| 2013/0141235 A1 | 6/2013 | Utter, II |
| 2014/0249160 A1 | 9/2014 | Miller |

FOREIGN PATENT DOCUMENTS

| | | |
|---|---|---|
| WO | 2011/147589 A1 | 12/2011 |
| WO | 2016/168486 A1 | 10/2016 |

OTHER PUBLICATIONS

Annex to the communication dated Mar. 19, 2019 for EP Application No. 16720614.
Article 94 (3) for Application No. 16720614.3, dated Nov. 19, 2019, 4 pages.
Communication from the Examining Division dated Aug. 30, 2018 for EP Application No. 16720614.
Europe Patent Application No. 16720614.3, Communication pursuant to Rules 161(1) and 162 EPC, dated Nov. 23, 2017, 2 pages.
Europe Patent Application No. 16720614.3, Examination Report, dated Aug. 30, 2018, 6 pages.
Intention to Grant for European Application No. 16720614.3 dated Mar. 11, 2020, 9 pages.
International Application No. PCT/US2016/027572, International Preliminary Report on Patentability, dated Oct. 17, 2017, 8 pages.
International Application No. PCT/US2016/027572, International Search Report, dated Jun. 3, 2016, 4 pages.
International Application No. PCT/US2016/027572, Written Opinion of the International Searching Authority, dated Jun. 3, 2016, 7 pages.
Non-Final Rejection dated Sep. 19, 2019 for U.S. Appl. No. 16/460,566.
Notice of Allowance and Fees Due (PTOL-85) dated Jan. 29, 2020 for U.S. Appl. No. 16/460,566.
Notice of Allowance for U.S. Appl. No. 15/564,644, dated Apr. 4, 2019, 5 pages.
Notice of Allowance for U.S. Appl. No. 15/564,644, dated Jun. 12, 2019, 4 pages.
Office Action for U.S. Appl. No. 15/564,644, dated Dec. 31, 2018, 13 pages.
Office Action for U.S. Appl. No. 15/564,644, dated Jun. 14, 2018, 13 pages.
Result of Consultation for European Application No. 16720614.3 dated Nov. 4, 2019, 3 pages.
Result of Consultation for European Application No. 16720614.3 dated Oct. 28, 2019, 3 pages.
Result of Consultation for European Application No. 16720614.3 dated Oct. 31, 2019, 4 pages.
Summons to Attend Oral Proceedings for European Application No. 16720614.3 dated Feb. 8, 2019, 9 pages.
Summons to Attend Oral Proceedings for European Application No. 16720614.3 dated Mar. 22, 2019, 2 pages.
Decision to grant a European patent dated Jul. 23, 2020 for EP Application No. 16720614.
Extended European Search Report dated Nov. 6, 2020 for EP Application No. 20190498, 8 pages.
U.S. Appl. No. 16/460,566, filed Jul. 2, 2019, 2019/0325727, Allowed.

* cited by examiner

MULTI-SENSOR INPUT ANALYSIS FOR IMPROVED SAFETY

CROSS-REFERENCE TO RELATED APPLICATIONS

This application is a continuation of U.S. patent application Ser. No. 16/460,566, filed on Jul. 2, 2019 and entitled "Multi-Sensor Input Analysis for Improved Safety," which is a continuation of U.S. patent application Ser. No. 15/564,644, filed on Oct. 5, 2017 and entitled "Multi-Sensor Input Analysis for Improved Safety," which claims priority to International Application No. PCT/US2016/027572, filed on Apr. 24, 2016 and entitled "Multi-Sensor Input Analysis for Improved Safety," which claims priority to and the benefit of foreign Indian Provisional Patent Application Serial No. 1065/DEL/2015, filed on Apr. 16, 2015 with the Government of India Patent Office and entitled "Multi-Sensor Input Analysis for Improved Safety," the entire disclosure of each of which is hereby incorporated herein by reference in its entirety for all purposes.

BACKGROUND

Workers or individuals at a facility can encounter various hazards such as toxic gases, noise, and the like. The workers can generally use person protective equipment (PPE) to protect against anticipated hazards. However, in some instances, the anticipated hazards may not be present, and the PPE used may then hinder the worker's performance due to the relatively cumbersome nature of PPE.

SUMMARY

In an embodiment, a method of limiting noise damage to an individual includes receiving, by an ototoxicity application stored in a non-transitory memory and executed on a processor, a first individual exposure level to a first ototoxic condition in an area, correlating the first individual exposure level to an ototoxic effect, determining a noise level threshold based on the correlating, receiving a noise level exposure in the area, comparing the noise level threshold with the noise level exposure, and sending an alert when the noise level exposure exceeds the noise level threshold. The noise level threshold is below a standard noise level threshold.

In an embodiment, a method of limiting noise damage to an individual comprises: receiving, by an ototoxicity application stored in a non-transitory• memory and executed on a processor, a plurality of exposure values for a plurality of chemicals in an area, correlating, by the ototoxicity application, the plurality of exposure values to an ototoxic effect, determining, by the ototoxicity application, a noise level reduction threshold based on the ototoxic effect, determining, by the ototoxicity application, an individual noise level threshold, receiving, by the ototoxicity application, a noise level exposure in the area for the individual, comparing the noise level threshold with the noise level exposure, and sending an alert when the noise level exposure exceeds the noise level threshold. The individual noise level threshold is reduced from a standard noise level threshold by at least the noise level reduction.

In an embodiment, a method of determining a compliance plan comprises determining, by a management application stored in a non-transitory memory and executed on a processor, a first exposure level to at least one condition within an area for a first time period, developing, by the management application, a first compliance plan based on the first exposure level for the first time period, determining, by the management application, a second exposure level to the at least one condition within the area for a second time period, and developing, by the management application, a second compliance plan based on the second exposure level for the second time period, wherein the second compliance plan is different than the first compliance plan. The second exposure level is different than the first exposure level.

These and other features will be more clearly understood from the following detailed description taken in conjunction with the accompanying drawings and claims.

BRIEF DESCRIPTION OF THE DRAWINGS

For a detailed description of the preferred embodiments of the invention, reference will now be made to the accompanying drawings in which.

DETAILED DESCRIPTION

Figure 1:
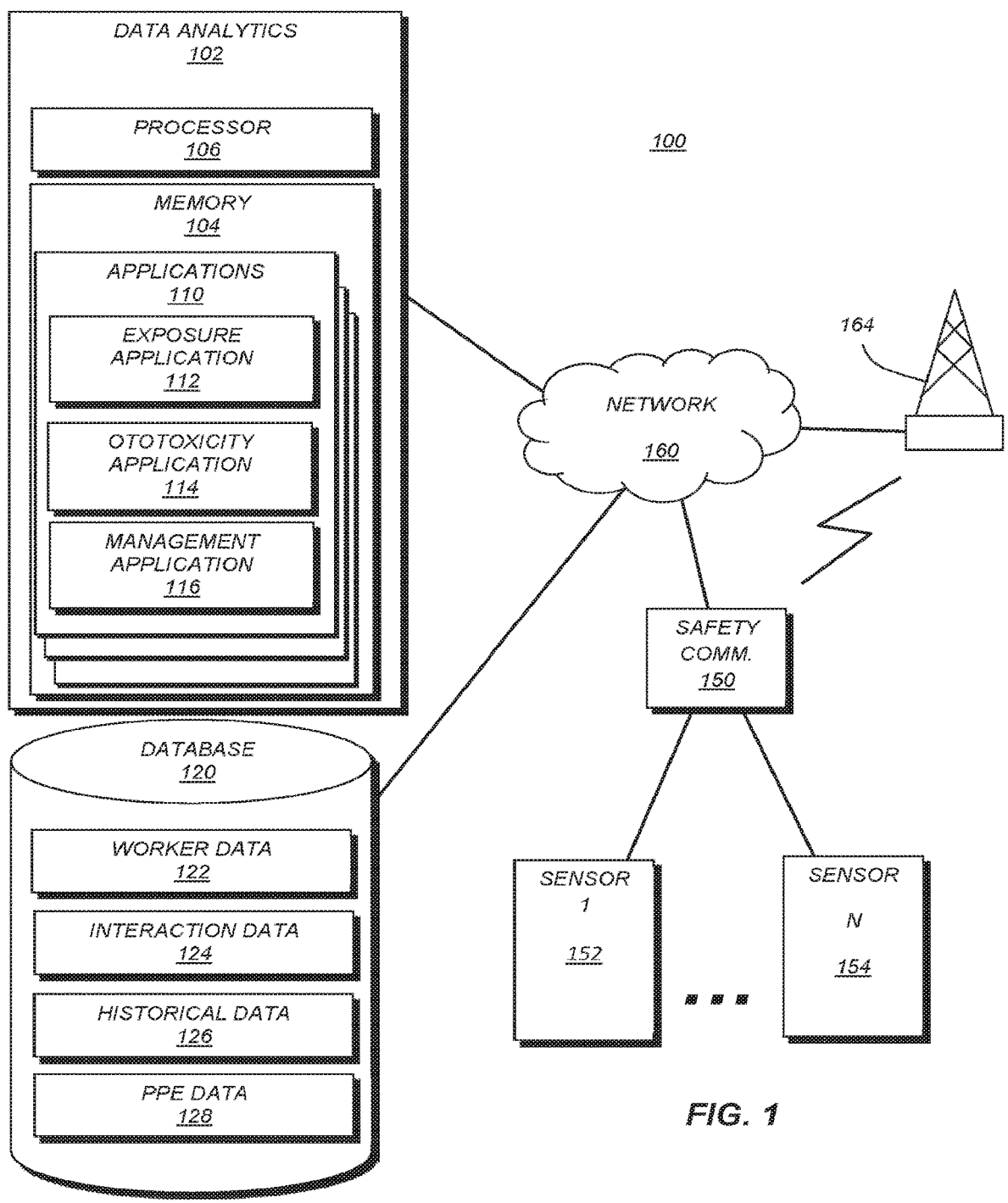
FIG. 1 is a schematic diagram of a multi-sensor system according to an embodiment.

It should be understood at the outset that although illustrative implementations of one or more embodiments are illustrated below, the disclosed devices, systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

In an embodiment, a workplace safety system may allow a plurality of sensors associated with environmental, location, and biometric information to be used to provide an integrated safety solution for one or more workers. A number of sensors can be employed, and the data from the sensors can be combined to provide a better view of the personal safety of the workers. For example, data from fixed and/or mobile sensors can be used to detect chemical components of an environment, environmental conditions (e.g., temperature, pressure, wind speed, wind direction, etc.), vibration levels, noise levels, biometric parameters (e.g., heart rate, body temperature, respiration rate, etc.), location (e.g., including 2-dimensional and/or 3-dimensional position), and the like. The resulting data can be relayed through a communication module to a server, where the data can be combined to provide an overall view of a workers risk factor. Various information such as alarms, notifications, information (e.g., maintenance protocols, instructions, live help, etc.), and the like can be relayed back to the worker through the system. The system may provide for better personal safety as a result of real time or near real time updates, improved productivity through the processing of multiple types of data, and better worker compliance with safety protocols by providing real time or near real time monitoring of personal protective equipment use, qualifications, and training for a variety of activities. All of these systems provide feedback to the worker to improve productivity, compliance, and safety in ways that have not previously been as efficient.

In a first example, ototoxicity in an environment can be monitored using multiple sensors. Ototoxicity can result from a combination of environmental factors, where any individual factor may be below an acceptable threshold, but when combined, the factors may result in injury to a worker.

Examples include hearing damage due to certain medications, exposure to certain workplace chemicals, age, medical conditions, and/or hereditary• conditions. In an embodiment, a worker's environment can be monitored using noise sensors, vibration sensors, and chemical sensors to determine an exposure level of the worker to environmental conditions. In some embodiments, the sensors can be configured to measure a sound level at a worker's ear to thereby take into account any hearing protection and additional sources of noise such as radio communications broadcast within a headphone. The sensors can be portable sensors associated with the worker and/or the sensors can be stationary• sensors associated with a workplace. A database may store information about the worker including any known medications and/or hereditary conditions. The information from the sensors can be communicated to a server configured to combine the sensor information with the personal information for the worker and develop a risk index using an ototoxicity correlation. The resulting risk index can be used to determine a reduction in a standard noise exposure level of the individual. For example, the standard noise exposure level may be reduced by a certain decibel level or a certain percentage for the individual based on the individual risk factors. For example, when a combination of environmental chemical exposure and/or chemicals taken for medical use are present, the system may determine an acceptable noise level based on the risk index and/or a standard threshold. The acceptable noise level can be below a standard acceptable noise level. When a noise level sensor associated with the worker detects a noise level above the individual threshold, an alert or notification can be sent to the worker to leave the area or use appropriate equipment (e.g., ear plugs, etc.). A mapping of a facility can also be performed when sufficient spatial information is available, and a worker can proactively be warned not to enter certain areas based on the combined effects of the exposure to chemicals and/or noise. The type of equipment used by the worker can be taken into account in this analysis. In some embodiments, the system may suggest the appropriate equipment, which may be more than the standard safety equipment. This personal recommendation may increase the workers productivity by avoiding having the worker return to a safety area to exchange their equipment during the performance of a job.

In a second example, the system may use multiple sensors and/or sensor types to provide a real time or near real time compliance plan for workers•. In general, the workplace safety plans are based predicting exposure levels and the necessary equipment for workers prior to a job. For example, the levels can be predicted at the beginning of each day or the beginning of each shift. By using multiple sensors, the protective equipment types can be tailored to a particular job at the time of the job and/or during its duration. For example, environmental sensors can be used to predict the environmental exposure of workers in an area of a facility based on the wind direction and speed, ambient chemical levels, etc. For example, workers performing a procedure in a plant may be exposed to a chemical level above a threshold at the job site during a first shift as a result of a first wind direction. The equipment needed by the workers may be determined by the exposure level. For example, in a first shift, workers may need respirators due to the presence of toluene at a particular job location. When a second shift occurs, the wind direction may have changed resulting in a lower exposure level of the ambient chemicals. While the same equipment may be used without sensor data, the use of multiple sensors (e.g., environmental sensors such as wind direction, wind speed, atmospheric pressure sensors, temperature sensors along with chemical sensors and worker location sensors) may allow different equipment to be used. For example, if the lower exposure level is below a threshold. a respirator may not be needed. The lower equipment standards may allow more freedom of movement to allow the workers to be more productive while not consuming equipment resources. The system may be dynamic and continually monitor the environment. If the wind direction changes, an alert or notification can be used to indicate that the workers should use the appropriate equipment or leave the area.

Referring to FIG. 1, a system 100 for providing workplace safety based on a combination of sensor inputs is illustrated. As shown in FIG. 1, the system may comprise a plurality of sensors 152, 154 in signal communication with a safety communicator 150. The safety communicator may provide a data connection to a data analytics server 102, a database 120 through a network 160. The safety communicator 150 may be wirelessly coupled to the network through an access point such as a Wi-Fi, Bluetooth, or cellular connection (e.g., through a wireless service tower 164).

In the system 100, the network 160 may be the Internet representing a worldwide collection of networks and gateways that use the Transmission Control Protocol/Internet Protocol (TCP/IP) suite of protocols to communicate with one another. In some embodiments, the system 100 may also be implemented as a number of different types of networks such as, for example, an intranet, a local area network (LAN), or a wide area network (WAN). FIG. 1 is intended as an example and not as an architectural limitation for varying embodiments.

The data analytics server 102 can comprise a memory 104, a processor 106, and one or more applications 11.0 stored in the memory that can configure the processor 106 to perform certain functions. In general, the data analytics server 102 is configured to receive sensor data such as ambient chemical concentrations, biometric data, environmental data, and/or location data associated with a worker and/or one or more sensors and process the data to provide information to the worker and/or decision makers at a facility. The data analytics server 102 is in communication with a database 120 that serves to store information used within the system 100. The database 120 can include a worker data store 122, an interaction data store 124, a historical data store 126 and/or a personal protective equipment (PPE) store 128.

The applications 110 can include an exposure application 112, an ototoxicity application 114, and/or a management application 116. Each application can communicated with one or more of the sensors 152, 154 and/or the safety communicator 150. The exposure application 112 can receive the sensor data, combine a plurality of the sensor inputs to detect a hazardous or potentially hazardous condition within a location (e.g., within one or more areas of a facility) and provide information to the safety communicator 150 and/or one or more sensors 152, 154. For example, the information can include alerts, notifications, information for performing a procedure, or the like.

In an embodiment, the exposure application 112 can receive a plurality of inputs from the sensors. As described in more detail below, the sensors can measure ambient chemical concentrations, location information, environmental information, biometric information from one or more individuals, noise levels, and the like. The sensor data can be stored in the historical data store 126 and used with the system. The exposure application 112 can use the sensor data along with the location data for the sensors to develop an exposure mapping of a facility. For example, a model can be used to predict the exposure at one or more locations within the facility, and the prediction can include areas where sensors are not present. The exposure values can be determined for various environmental hazards including chemical exposure, noise exposure, light and heat exposure and the like.

Once the exposure application 112 has determined exposure levels within a facility, the exposure values for a number of environmental hazards can be combined to provide a better view of the personal safety of the workers. For example, data for a chemical exposure as well as a noise exposure at a given location can be used to determine potential ototoxicity effects at that location. Various information and statistical models can be used to determine the interactions between various parameters. The interaction data can be stored in the interaction data store 124 and accessed by the exposure application 1.12 as part of the determination of the risk value or rating at each location. The risk values can be determined at various locations within a facility, and a risk value mapping can be created. The resulting data can be stored in the historical data store 126.

The measurement and exposure determination process can be repeated periodically by the exposure application 112. For example, the exposure application may update the exposure values at an interval of less than one minute, less than five minutes, less than thirty minutes, or less than an hour. The rate at which the exposure values and/or the risk value rating are updated may be based, at least in part, on the rate at which the sensor data (e.g., sensor values, location data, etc.) is updated and communicated back to the data analytics server 102.

In some embodiments, the exposure application 112 may monitor the risk value with respect to the location of one or more individuals and provide feedback to a manager and/or the individuals based on the risk value associated with the individual's location and/or expected location based on predicted movements. The risk value can be determined based on a base case for an individual without any PPE, or in some embodiments, an individual's PPE selection can be stored in the worker data store 122 and included in the determination of the risk value. Using the plurality of sensor readings (with or without the PPE considerations) to arrive at the risk value may allow a workers current risk to be evaluated and communicated to each worker.

When a worker is at a location at which the risk value exceeds a threshold, an alert, an alarm, a notification, and/or information (e.g., maintenance protocols, instructions, live help, etc.), and the like can be relayed back to the worker through the system. For example, the data analytics server 102 may send a message to the safety communicator 150 to display the information. The alerts can indicate the level of risk, a notification that additional PPE is required, or an indication that the individual should not enter a specified area or leave an area if the individuals are already within the area. The ability to update the data and determine the risk value in real time or near real time may provide for better personal safety as a result of real time or near real time updates, improved productivity through the processing of multiple types of data, and better worker compliance with safety protocols by providing real time or near real time monitoring of personal protective equipment use, qualifications, and training for a variety of activities.

The safety communicator 150 may interact with one or more sensors to provide the information to the system 100. The sensors can include sensors associated with an individual and/or facility sensors. In general, the individuals may wear one or more personal protection equipment (PPE) devices for detection and communication. For example, a person may wear a portable gas detector operable to identify gases in the air and determine the levels of gases in the environment. Also, a person may wear any number of monitoring devices that may monitor movement, breathing, heart rate, etc. Additionally, personnel may wear portable location devices operable to communicate the location of the device (and therefore the user) to a central monitoring station. These portable devices may communicate wirelessly, over a wireless fidelity (Wi-Fi) network, via Bluetooth, or another wireless connection.

In some embodiments, a noise sensor can be associated with an individual or worker. The noise sensor may be configured to detect an ambient noise level and/or a personalized noise level. As an example of a personalized noise level, the noise sensor can be placed at or near the individual's ear to measure the noise level reaching the ear. In some embodiments, the noise sensor can be placed at or near the individual's ear within a hearing protection device. When a speaker or other noise source is placed within the hearing protection device, the noise sensor may then sense both the ambient noise passing through the hearing protection device and the noise generated by any such speaker or noise source. For example, an individual may wear hearing protection in the form of ear muffs that can reduce the ambient noise level. The noise sensor can be placed within the ear muffs near the individual's ear. If a radio speaker is included in the ear muff to allow for communication with other devices, the noise sensor may then detect the noise level at the individual's ear including the noise projected by the speaker. Such a placement of a noise sensor may allow an individual's noise exposure to be accurately determined and recorded over time.

Facility sensors, which may be stationary within a facility, may also be present. The stationary sensors can measure any of the information that the portable and personal sensors can measure. The stationary sensors may also measure information such as environmental data (e.g., pressure, temperature, wind speed, wind direction, etc.). The facility sensors may communicate wirelessly and/or through a wired connection to the data analytics server 102 to provide data used with the applications 110.

In some cases, the multiple PPE devices associated with an individual may have alarms, notifications, or updates that are communicated to the user via sounds, vibrations, or visual notifications. In some embodiments, each PPE device may communicate individually with the central monitoring station, employing multiple wireless infrastructures. In some embodiments, a safety communicator (e.g., a communication device) comprising a processor and memory to enable data collection and communication applications may be used to collect the sensor data and communicate the sensor data to the various elements of the system 100. For example, the application may establish a connection between a smartphone and each of the PPE devices, which may be wireless connections, such as Wi-Fi or Bluetooth. The application may then receive data from each of the PPE devices, and store the data locally on the device. The application may also transfer the data to a cloud storage network via a cellular network. Additionally, the application may communication the combined data from all of the PPE devices to the central monitoring station. The application may automatically receive data from the PPE devices and send the data to the data analytics server 102. Additionally, the application may be operable to send messages or calls to other safety communicators associated with other individuals if needed, such as in an alarm or emergency situation.

The application on the safety communicator may present information to the user via a user interface on the smartphone or connected to the smartphone (such as a smartwatch). The interface may compile the information received from each of the PPE devices into a consistent format, making it easier to read and understand. The user may be able to adjust alarm limits and settings in the application. The application may show real-time readings via the user interface, and may issue alerts or warnings via the user interface. Additionally, vibrations or audible alerts may also be issued by the application via the smartphone. In some cases, the application may be operable to communicate with a headset or earpiece (such as a Bluetooth headset for example) worn by the user to communicate audible alerts or warnings.

The sensors can detect various types of information such as chemical components of an environment, environmental conditions (e.g., temperature, pressure, wind speed, wind direction, etc.), vibration levels, noise levels (e.g., ambient noise levels, noise levels at or near an individual's ear, etc.), biometric parameters (e.g., heart rate, body temperature, respiration rate, etc.), location (e.g., including 2-dimensional and/or 3-dimensional position), and the like. The chemical sensors can be detected using various types of gas sensors. The gas detectors may include, but are not limited to, radiation detectors, smoke detectors, and detectors for determining abnormally low oxygen content in the atmosphere, as well as a wide variety of detectors for detecting chemically hazardous or flammable gases such as, for example, hydrogen sulfide, ammonia, carbon monoxide, natural gas, phosgene, organic compounds (e.g., volatile organic compounds, etc.), and so forth. The gas sensors can also be configured to include integrated wireless communications and the ability to periodically and under event conditions, report the location information, time information, and gas concentration level information wirelessly.

The use of multiple exposure values to determine a risk value may find applications in several areas. In some environments, the exposure to multiple environmental hazards can result in a synergistic effect to cause harm to an individual at a level below one or more acceptable exposure thresholds for the individual hazards. By using specific correlations for the known synergistic interactions, the risk value can be calculated using the system 100 to prevent inadvertent harm to an individual.

In an embodiment, the combined effects of an individual being exposed to various hazards can find application to avoid potential ototoxic effects. In general, ototoxicity refers to the property of being toxic to the ear, which can result in reversible or temporary hearing loss, or in some cases irreversible or permanent hearing loss. Various ototoxic conditions exist that can result in a lowering of the threshold for a noise exposure that can result in temporary and/or permanent hearing loss. The ototoxic conditions can comprise certain chemical exposures that can lower the threshold for the exposure to noise at which hearing loss occurs. For example, some pharmaceutical compositions can result in a reduced noise level threshold at which hearing loss occurs. The ototoxic conditions can also comprise other environmental chemical exposures such as exposures to organic solvents such as toluene, styrene, and/or xylene can lower the noise level exposure threshold at which hearing loss occurs. The ototoxic conditions can also include various environmental parameters (e.g., temperature, pressure, etc.), and physiological parameters (e.g., age, medical conditions, baseline hearing levels, and the like). By detecting and combining the potential exposures to the ototoxic conditions, the system 100 can provide a dynamic noise exposure level for an individual.

In some embodiments, the exposure application 112 can perform the determination of the potential ototoxic effects. In some embodiments, a separate ototoxicity application 114 may work alone or in combination with the exposure application 112 to determine the dynamic threshold. When an ototoxicity application 114 is used, the ototoxicity application 114 may access information in the interaction data store 124 to determine the identity of various ototoxic conditions such as chemical compounds, environmental parameters (e.g., temperature, pressure, etc.), and physiological parameters (e.g., age, medical conditions, baseline hearing levels, and the like) as well as one or more correlations for determining the effects of exposure to the ototoxic conditions on the allowable noise exposure levels. The ototoxicity application 114 may also access the worker data store 122 to retrieve personal information about each individual such as current medications, hereditary conditions associated with hearing loss, other medical data, current PPE being used, and the like. In some embodiments, baseline hearing levels can be measured initially and/or over time to determine a baseline hearing level for determination of the threshold. The individuals may provide the worker data to the worker data store 122 prior to their presence within the facility. For example, workers can provide background medical information before starting their employment, before each shift, or at some other time. The individuals may also log the type of PPE equipment being used automatically or manually. For example, the safety communicator 150 may be capable of detecting the presence of various PPE as well as compliance with the proper use of the PPE equipment by the individual within the facility. PPE information for each of the PPE being used can be obtained from the PPE data store 128 for use with the ototoxicity application 114. For example, hearing protection may be detected by the safety communicator 150 including the proper positioning of the hearing protection as well as a model number or other identifier for the hearing protection. Using the identifier, the noise level reduction of the hearing protection can be retrieved from the PPE data store 128 and used in the determination of the individual exposure threshold. In some embodiments, the noise level can be measured at or near one or both ears of an individual and compared to an ambient noise level to determine if the proper noise reduction is being achieved by the hearing protection. If the hearing protection is insufficient, additional PPE can be suggested, warnings can be generated, or the like.

The ototoxicity application 114 may interact with the exposure application 112 by obtaining the determination of the exposure values to each of the environmental hazards and applying the ototoxic correlations at a given point to obtain an overall acceptable noise level threshold for an individual. For example, the exposure application 112 may determine an exposure to toluene at various locations within a facility. The toluene exposure level can be combined with any pharmaceutical information obtained from the worker data store 122, along with the individual's statistics (age, baseline hearing level, any hereditary conditions, etc.) for an individual to determine a reduction in the standard acceptable noise exposure threshold. The acceptable noise level can then be compared with an individual's current position using position information from the safety communicator and a noise level at the individual's ear and/or ambient noise levels to determine if the individual is being exposed to a noise level above a dynamic threshold. If the system indicates that the individual is using PPE, the PPE information can be used in the determination of the dynamic threshold.

The ototoxicity application 114 may provide a dynamic mapping of a facility to determine if any areas have unacceptable noise levels for an individual. Using the mapping or predictions provided by the exposure application 112, the ototoxicity application 114 can determine the acceptable thresholds throughout an area. The information about the individual can be included in this determination in order to provide a dynamic, personalized noise threshold value for each individual. For example, if a first individual is on a medication having ototoxic effects, the acceptable noise threshold for the first individual may be less than the noise threshold for a second individual not taking the medication. The acceptable noise levels as well as alerts and notifications can be sent from the ototoxicity application 114 to the safety communicator 150 for display to each individual. In some embodiments, the acceptable threshold and/or mapping can be sent to the safety communicator 150 and/or a noise sensor, which can perform the dynamic monitoring for the individual.

The ototoxicity application 114 may proactively use the ototoxicity determination in the facility to suggest or require certain PPE for an individual. This determination may be individualized for each person present within a facility based on the expected exposure and the individual's personal information. For example. the ototoxicity application 114 may access the historical data 126 to obtain a maximum expected noise level and/or chemical exposure level within an area or facility. Using this information along with the individual data in the worker data store 122, the system 100 may determine the level of noise reduction required for an individual and recommend one or more types of PPE for the individual. If the noise level cannot be reduced to avoid potential hearing loss, an individual may be warned not to enter certain high noise areas. In some embodiments, the ototoxicity application 114 may recommend PPE associated with reducing the exposure to the chemicals resulting in the ototoxic effects. For example, a respirator may be recommended for a first individual taking a medication having an ototoxic effect while not recommending a respirator for a second individual who is not taking any medications with ototoxic effects. During use when a noise sensor is placed at or near the ear of the individual, the noise reduction due to the PPE (e.g., hearing protection, mask, etc.) can be directly monitored by monitoring the noise level reaching the ear. If the noise level rises above a personalized threshold based on the ototoxicity conditions, a warning can be generated to warn the individual to leave the area. In some embodiments, a subsequent hearing test can be conducted to determine if any short term and/or long term hearing loss results .from an exposure over a threshold.

In order to enforce this policy, the sensors may detect compliance with the PPE requirements and/or use location determinations in order to monitor the exposure of an individual to a noise level above the individualized threshold. If the policy is violated, an alert can be sent to the individual (e.g., using a graphical user interface on the safety communicator 150) and/or a management application 116 to alert a supervisor to a potential safety violation. Corrective action can then be taken based on the alerts.

The ototoxicity application 114 may provide updated thresholds in real time or near real time. Using the data as updated by the exposure application 112, the ototoxic determination can be updated for each individual within an area. The updated information can include information specific to the chemical exposure, the noise level exposure, and/or any updates to the PPE used by the individual. Thus, the system 100 can provide an individualized exposure level that is dynamic in nature and is based on using multiple types of sensor data. in this way the synergistic effects of various environmental hazards can be determined to provide an increased level of safety for individuals. In some embodiments, the noise levels can be monitored and stored in an exposure log. The exposure log can be used to provide an integrated exposure value to the various ototoxic conditions, which may affect the dynamic threshold as the individual is exposed to various conditions over time.

In some embodiments, the ototoxicity application 114 may determine the dynamic threshold and the sound level generated within a PPE, for example by a communication device speaker or other noise source, can be dynamically adjusted to avoid exceeding the threshold. For example, the noise sensor placed at or near one or both ears can be used to provide a measure of an actual sound exposure level. The noise contribution of any such speaker or noise source can then be directly monitored. The volume of the speak and/or noise source can then be dynamically adjusted to avoid the total noise level at the ear exceeding a threshold. If the sound level would be adjusted below an audibly detectable level, a visual warning may be generated to indicate that an individual should leave an area to receive instructions or otherwise use additional hearing protection.

Over time, the sound exposure levels and ototoxic condition information can be stored in the historical data store 126 and/or worker data store 122. Baseline hearing tests can be performed to obtain additional information on potential hearing loss due to noise events exceeding a threshold. This information may be used to update the interaction data store 124. For example, if an individual is exposed to noise at or near a threshold, or over a threshold and hearing loss results, this information can be stored to adjust the thresholds for individual's under similar circumstances. Over time. this feedback mechanism may allow additional ototoxic conditions to be detected and accounted for in the ototoxicity application 114.

In another embodiment, multiple types of sensor data can be combined to provide real time or near real time compliance plans for individuals in an environment having exposure to various hazardous conditions. The compliance plans can be based on present and predicted conditions to provide a more accurate compliance plan. In an embodiment, the measurements of exposure values can be more accurately predicted by combining the exposure value data with environmental information. The resulting exposure values can then be used to develop the compliance plan, and the updated exposure values can be used to provide real time or near real time updates to the compliance plan. If the compliance plan is insufficient based on the actual measurements, an alert or other notification can be issued to notify individuals of the change.

In order to prepare the compliance plan, a management application 116 can execute on the processor 106 of the data analytics server 102. The management application 116 can interact with the exposure application 112 to obtain exposure values 112 and/or an exposure mapping for one or more of the conditions. The management application 116 may access the information in the historical data store 126 to develop a model for predicting the expected exposure to individuals for a certain time period. For example, the management application 116 may access the historical data store 126 to determine the expected exposure to various chemicals in an area. The information in the historical data store 126 may be used to provide peak exposure values, provide a correlation or model for determining exposures based on environmental conditions such as wind speed and wind direction, or provide a repository of the sources of the conditions (e.g., a chemical leak source, noise level source, etc.). The management application 11.6 may combine the information to determine an expected or predicted exposure for an area.

The management application 116 may use the predicted values to determine a compliance plan for the time period. The compliance plan may generally provide the appropriate PPE and/or other safety measures needed in accordance with various standards based on the expected exposure levels for a location. For example, the compliance plan may specify the type of PPE to be used by an individual for the areas the individual is expected to visit. The compliance plan may specify the PPE based on the peak exposure of one or more chemicals during the exposure period. For example, an individual being exposed to a volatile organic compound may be required to wear a respirator if the exposure level is above a threshold.

The compliance plan can change between exposure time periods, and in some embodiments, the compliance plan can be updated in real time or near real time. Since the compliance plan is prepared by the management application 116 based on the expected exposure amounts, the compliance plan can change when the expected exposure changes. For example, a higher exposure to volatile organic compounds can be expected when an individual is in an area being painted due to the chemicals emitted from the paint as it dries. At a later time when the paint has dried, the exposure to the volatile organic chemicals in the area may be significantly lower. The compliance plan may call for a respirator during the first time while not requiring a respirator at the second time.

In some embodiments, the compliance plan can be updated in real time or near real time. The ability to update the compliance plan may allow for dynamic compliance plans. In general, the compliance plan may be based on expected exposure values with a certain prediction period. For example, the prediction period may be at least about five minutes, at least about ten minutes, or at least about thirty minutes. The prediction period may allow for changes to the compliance plan to be implemented in a reasonable amount of time. For example, if the compliance plan shifts from not needing a respirator to requiring a respirator, a suitable amount of time may be needed for the respirator to be obtained and used by an individual.

In some embodiments, the management application 116 may provide a compliance mapping of an area to provide compliance plans for different areas based on the varying exposure levels. For example, a mapping may be provided to indicate the areas that will require respirators, noise protection, and the like. The mapping may be used to correlate a compliance plan with an individual's expected location during a time period.

As an exemplary use of the system 100, the management application 116 may determine an environmental exposure to one or more chemicals using various measurements including environmental conditions. For example, based on the wind speed, wind direction, and ambient levels of a chemical, the management application 116 may determine that an individual working a location may be exposed to a first level of a chemical. For example, an individual may be exposed to a first level of an organic compound at a first time. A compliance plan for the first time period can then be prepared by the management application 116. At a later time, the management application 116 may prepare a second compliance plan. In order to prepare the second compliance plan, the management component 116 may obtain the expected exposure values from the exposure application 112 and/or the historical data store 126. The management application 116 may take various factors such as the wind speed and direction, the ambient levels of various chemicals, the noise levels with the area, and the like in order to prepare the second compliance plan. The plurality of sensor readings can be combined in order to prepare an estimate of the exposure levels during the second time period. Based on the expected exposure levels, the second compliance plan can be determined by the management component 116. For example, due to a wind direction change during the second time period, the expected exposure to the organic compound may be reduced to a second level. Due to the reduction in the exposure, the compliance plan may indicate that certain PPE is not required during the second time period.

The system 100 may continue to update the expected exposure values and provide an update to the compliance plan. The updated compliance plan can be checked against the current individual's location, PPE usage, training, and the like to determine if the individual is complying with the updated compliance plan. If the updated compliance plan is violated, a notification, alert, warning, or other indication can be sent to the individual (e.g., to the safety communicator 150) and/or a manager or supervisor. The indication may provide updated requirements for working in the affected areas. The ability to have a compliance plan that is updated may allow for improved productivity and safety for the individuals working in affected areas.

Figure 2:
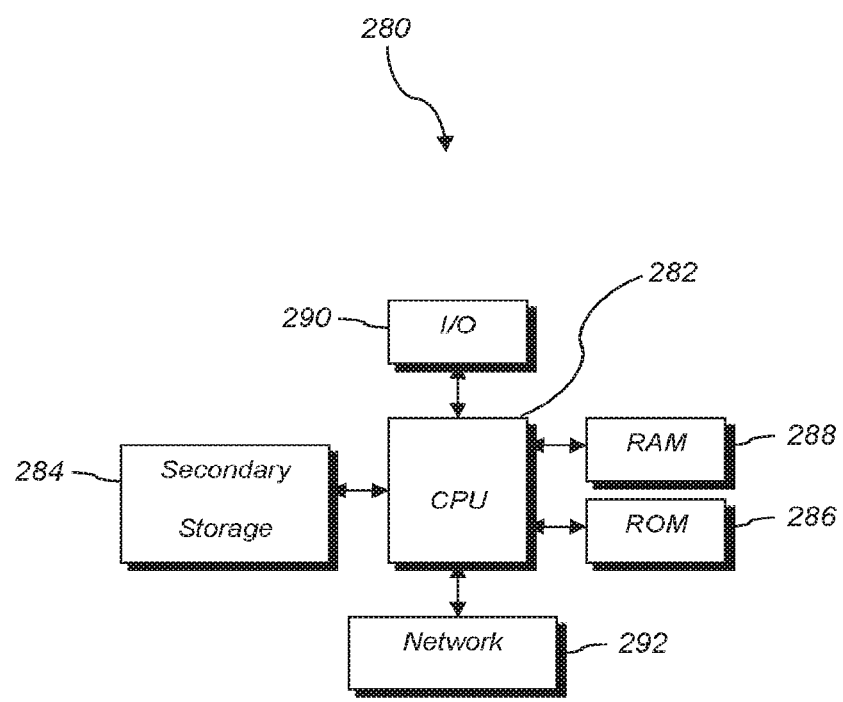
FIG. 2 schematically illustrates a computer that can be used to carry out various steps according to an embodiment.

Any of the systems and methods disclosed herein can be carried out on a computer or other device comprising a processor, such as the communication device 150, the data analytics server 102, any of the sensors 152, 154, and/or the database 120 of FIG. 1. FIG. 2 illustrates a computer system 280 suitable for implementing one or more embodiments disclosed herein such as the acquisition device or any portion thereof. The computer system 280 includes a processor 282 (which may be referred to as a central processor unit or CPU) that is in communication with memory devices including secondary storage 284, read only memory (ROM) 286, random access memory (RAM) 288, input/output (110) devices 290, and network connectivity devices 292. The processor 282 may be implemented as one or more CPU chips.

It is understood that by programming and/or loading executable instructions onto the computer system 280. at least one of the CPU 282. the RAM 288, and the ROM 286 are changed, transforming the computer system 280 in part into a particular machine or apparatus having the novel functionality taught by the present disclosure. It is fundamental to the electrical engineering and software engineering arts that functionality that can be implemented by loading executable software into a computer can be converted to a hardware implementation by well-known design rules. Decisions between implementing a concept in software versus hardware typically hinge on considerations of stability of the design and numbers of units to be produced rather than any issues involved in translating from the software domain to the hardware domain. Generally, a design that is still subject to frequent change may be preferred to be implemented in software, because re-spinning a hardware implementation is more expensive than re-spinning a software design. Generally, a design that is stable that will be produced in large volume may be preferred to be implemented in hardware, for example in an application specific integrated circuit (ASIC), because for large production runs the hardware implementation may be less expensive than the software implementation. Often a design may be developed and tested in a software form and later transformed, by well-known design rules, to an equivalent hardware implementation in an application specific integrated circuit that hardwires the instructions of the software. In the same manner as a machine controlled by a new ASIC is a particular machine or apparatus, likewise a computer that has been programmed and/or loaded with executable instructions may be viewed as a particular machine or apparatus.

Additionally, after the system 280 is turned on or booted, the CPU 282 may execute a computer program or application. For example, the CPU 282 may execute software or firmware stored in the ROM 286 or stored in the RAM 288. In some cases, on boot and/or when the application is initiated, the CPU 282 may copy the application or portions of the application from the secondary storage 284 to the RAM 288 or to memory space within the CPU 282 itself, and the CPU 282 may then execute instructions that the application is comprised of In some cases, the CPU 282 may copy the application or portions of the application from memory accessed via the network connectivity devices 292 or via the I/O devices 290 to the RAM 288 or to memory space within the CPU 282, and the CPU 282 may then execute instructions that the application is comprised of During execution, an application may load instructions into the CPU 282, for example load some of the instructions of the application into a cache of the CPU 282. In some contexts, an application that is executed may be said to configure the CPU 282 to do something, e.g., to configure the CPU 282 to perform the function or functions promoted by the subject application. When the CPU 282 is configured in this way by the application, the CPU 282 becomes a specific purpose computer or a specific purpose machine.

The secondary storage 284 is typically comprised of one or more disk drives or tape drives and is used for non-volatile storage of data and as an over-flow data storage device if RAM 288 is not large enough to hold all working data. Secondary storage 284 may be used to store programs which are loaded into RAM 288 when such programs are selected for execution. The ROM 286 is used to store instructions and perhaps data which are read during program execution. ROM 286 is a non-volatile memory device which typically has a small memory capacity relative to the larger memory capacity of secondary storage 284. The RAM 288 is used to store volatile data and perhaps to store instructions. Access to both ROM 286 and RAM 288 is typically faster than to secondary storage 284. The secondary storage 284, the RAM 288, and/or the ROM 286 may be referred to in some contexts as computer readable storage media and/or non-transitory computer readable media.

I/O devices 290 may include printers, video monitors, liquid crystal displays (LCDs), touch screen displays, keyboards, keypads, switches, dials, mice, track balls, voice recognizers, card readers, paper tape readers, or other well-known input devices.

The network connectivity devices 292 may take the form of modems, modem banks. Ethernet cards, universal serial bus (USB) interface cards, serial interfaces, token ring cards, fiber distributed data interface (FDDI) cards, wireless local area network (WLAN) cards, radio transceiver cards that promote radio communications using protocols such as code division multiple access (CDMA), global system for mobile communications (GSM), longterm evolution (LTE), worldwide interoperability for microwave access (WiMAX), near field communications (NFC), radio frequency identity (RFID), and/or other air interface protocol radio transceiver cards, and other well-known network devices. These network connectivity devices 292 may enable the processor 282 to communicate with the Internet or one or more intranets. With such a network connection, it is contemplated that the processor 282 might receive information from the network, or might output information to the network (e.g., to an event database) in the course of performing the above-described method steps. Such information, which is often represented as a sequence of instructions to be executed using processor 282, may be received from and outputted to the network, for example, in the form of a computer data signal embodied in a carrier wave.

Such information, which may include data or instructions to be executed using processor 282 for example, may be received from and outputted to the network, for example, in the form of a computer data baseband signal or signal embodied in a carrier wave. The baseband signal or signal embedded in the carrier wave, or other types of signals currently used or hereafter developed, may be generated according to several methods well-known to one skilled in the art. The baseband signal and/or signal embedded in the carrier wave may be referred to in some contexts as a transitory signal.

The processor 282 executes instructions, codes, computer programs, scripts which it accesses from hard disk, floppy disk, optical disk (these various disk based systems may all be considered secondary storage 284), flash drive, ROM 286, RAM 288, or the network connectivity devices 292. While only one processor 282 is shown, multiple processors may be present. Thus, while instructions may be discussed as executed by a processor, the instructions may be executed simultaneously, serially, or otherwise executed by one or multiple processors. Instructions, codes, computer programs, scripts, and/or data that may be accessed from the secondary storage 284, for example, hard drives, floppy disks, optical disks, and/or other device, the ROM 286, and/or the RAM 288 may be referred to in some contexts as non-transitory instructions and/or non-transitory information.

In an embodiment, the computer system 280 may comprise two or more computers in communication with each other that collaborate to perform a task. For example, but not by way of limitation, an application may be partitioned in such a way as to permit concurrent and/or parallel processing of the instructions of the application. Alternatively, the data processed by the application may be partitioned in such a way as to permit concurrent and/or parallel processing of different portions of a data set by the two or more computers. In an embodiment, virtualization software may be employed by the computer system 280 to provide the functionality of a number of servers that is not directly bound to the number of computers in the computer system 280. For example, virtualization software may provide twenty virtual servers on four physical computers. In an embodiment, the functionality disclosed above may be provided by executing the application and/or applications in a cloud computing environment. Cloud computing may comprise providing computing services via a network connection using dynamically scalable computing resources. Cloud computing may be supported, at least in part, by virtualization software. A cloud computing environment may be established by an enterprise and/or may be hired on an as-needed basis from a third party provider. Some cloud computing environments may comprise cloud computing resources owned and operated by the enterprise as well as cloud computing resources hired and/or leased from a third party provider.

In an embodiment, some or all of the functionality disclosed above may be provided as a computer program product. The computer program product may comprise one or more computer readable storage medium having computer usable program code embodied therein to implement the functionality disclosed above. The computer program product may comprise data structures, executable instructions, and other computer usable program code. The computer program product may be embodied in removable computer storage media and/or non-removable computer storage media. The removable computer readable storage medium may comprise, without limitation, a paper tape, a magnetic tape, magnetic disk, an optical disk, a solid state memory chip, for example analog magnetic tape, compact disk read only memory (CD-ROM) disks, floppy disks, jump drives, digital cards, multimedia cards, and others. The computer program product may be suitable for loading, by the computer system 280, at least portions of the contents of the computer program product to the secondary storage 284, to the ROM 286, to the RAM 288, and/or to other non-volatile memory and volatile memory of the computer system 280. The processor 282 may process the executable instructions and/or data structures in part by directly accessing the computer program product, for example by reading from a CD-ROM disk inserted into a disk drive peripheral of the computer system 280. Alternatively, the processor 282 may process the executable instructions and/or data structures by remotely accessing the computer program product, for example by downloading the executable instructions and/or data structures from a remote server through the network connectivity devices 292. The computer program product may comprise instructions that promote the loading and/or copying of data, data structures, files, and/or executable instructions to the secondary storage 284, to the ROM 286, to the RAM 288, and/or to other non-volatile memory and volatile memory of the computer system 280.

In some contexts, the secondary' storage 284, the ROM 286, and the RAM 288 may be referred to as a non-transitory computer readable medium or a computer readable storage media. A dynamic RAM embodiment of the RAM 288, likewise, may be referred to as a non-transitory computer readable medium in that while the dynamic RAM receives electrical power and is operated in accordance with its design, for example during a period of time during which the computer system 280 is turned on and operational, the dynamic RAM stores information that is written to it. Similarly, the processor 282 may comprise an internal RAM, an internal ROM, a cache memory, and/or other internal non-transitory storage blocks, sections, or components that may be referred to in some contexts as non-transitory computer readable media or computer readable storage media.

While a number of systems and methods have been described herein, specific embodiments can include, but are not limited to:

In a first embodiment, a method of limiting noise damage to an individual comprises: receiving, by an ototoxicity application stored in a non-transitory memory and executed on a processor, a first individual exposure level to a first ototoxic condition in an area; correlating, by the ototoxicity application, the first individual exposure level to an ototoxic effect; determining, by the ototoxicity application, a noise level threshold based on the correlating, wherein the noise level threshold is below a standard noise level threshold; receiving, by the ototoxicity application, a noise level exposure in the area; comparing the noise level threshold with the noise level exposure; and sending an alert when the noise level exposure exceeds the noise level threshold.

A second embodiment can include the method of the first embodiment, further comprising: receiving, by the ototoxicity application, a second individual exposure level to a second ototoxic condition in an area; wherein the correlating further comprises correlating the first individual exposure level and the second individual exposure level to an ototoxic effect, wherein the determining of the noise level threshold comprises determining a second noise level threshold, wherein the second noise level threshold is below the noise level threshold.

A third embodiment can include the method of the second embodiment, wherein the ototoxic condition comprises an exposure to a chemical comprising a pharmaceutical compound taken by the individual.

A fourth embodiment can include the method of any of the first to third embodiments, further comprising: determining a personal protective equipment guideline based on the noise level threshold and the noise level exposure; and send the personal protective equipment guideline to the individual.

A fifth embodiment can include the method of any of the first to fourth embodiments, wherein the first individual exposure level is received from a gas sensor.

A sixth embodiment can include the method of any of the first to fifth embodiments, wherein the alert comprises instructions not to enter the area.

A seventh embodiment can include the method of any of the first to fifth embodiments, wherein the alert comprises instructions to leave the area.

An eighth embodiment can include the method of any of the first to seventh embodiments, wherein receiving the first individual exposure level comprises receiving an estimate of the first individual exposure level from a chemical exposure mapping of the area, wherein the chemical exposure mapping is determined from a plurality of sensor inputs within the area.

A ninth embodiment can include the method of any of the first to ninth embodiments, wherein receiving the noise level exposure comprises receiving, from a noise sensor associated with the individual, an noise level reading.

A tenth embodiment can include the method of the ninth embodiment, wherein the noise sensor detects the noise level at an ear.

An eleventh embodiment can include the method of any of the first to tenth embodiments, wherein the ototoxic condition comprises at least one of an exposure to a chemical in the environment, an exposure to a pharmaceutical composition, one or more environmental parameters, one or more physiological parameters, or any combination thereof.

In a twelfth embodiment, a method of limiting noise damage to an individual comprises: receiving, by an ototoxicity application stored in a non-transitory memory and executed on a processor, a plurality of exposure values for a plurality of chemicals in an area; correlating. by the ototoxicity application, the plurality of exposure values to an ototoxic effect; determining, by the ototoxicity application, a noise level reduction threshold reduction based on the ototoxic effect; determining, by the ototoxicity application, an individual noise level threshold, wherein the individual noise level threshold is reduced from a standard noise level threshold by at least the noise level reduction; receiving, by the ototoxicity application, a noise level exposure in the area for the individual; comparing the noise level threshold with the noise level exposure; and sending an alert when the noise level exposure exceeds the noise level threshold.

A thirteenth embodiment can include the method of the twelfth embodiment, further comprising: determining a personal protective equipment requirement for the individual based on the ambient noise level exposure and the individual noise level threshold, wherein the personal protective equipment requirement is configured to reduce the noise level exposure to below the individual noise level threshold.

In a fourteenth embodiment, a method of determining a compliance plan comprises: determining, by a management application stored in a non-transitory memory and executed on a processor, a first exposure level to at least one condition within an area for a first time period; developing, by the management application, a first compliance plan based on the first exposure level for the first time period: determining, by the management application, a second exposure level to the at least one condition within the area for a second time period, wherein the second exposure level is different than the first exposure level; developing, by the management application, a second compliance plan based on the second exposure level for the second time period, wherein the second compliance plan is different than the first compliance plan.

A fifteenth embodiment can include the method of the fourteenth embodiment, wherein determining the first exposure level comprises determining the first exposure level based on a plurality of sensor readings for a plurality of sensor.

A sixteenth embodiment can include the method of the fourteenth or fifteenth embodiment, wherein determining the first exposure level comprises determining the first exposure level based on a plurality of environmental conditions, wherein the environmental conditions comprise at least wind speed, wind direction, and ambient chemical concentrations.

A seventeenth embodiment can include the method of any of the fourteenth to sixteenth embodiments, wherein the second exposure level comprises receiving a plurality of sensor inputs from a plurality of sensors within the area.

An eighteenth embodiment can include the method of any of the fourteenth to seventeenth embodiments, further comprising: receiving a plurality of sensor inputs during the first time period; determining an updated exposure levels during the first time period based on the plurality of sensor inputs; comparing the updated exposure level to a threshold for the at least one condition; and sending an alert when the updated exposure level exceeds the threshold for the at least one condition.

A nineteenth embodiment can include the method of any of the fourteenth to eighteenth embodiments, wherein the at least one condition comprises an exposure to a chemical compound, an exposure to a noise level, an exposure to a vibration level, or an exposure to a first height level.

A twentieth embodiment can include the method of any of the fourteenth to nineteenth embodiments, wherein the compliance plan comprises one or more requirements for personal protective equipment based on the first exposure level.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may' be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. An apparatus comprising:
a processor; and
a memory storing an ototoxicity application, wherein the ototoxicity application is operable, when executed by the processor, to cause the processor to:
determine, based on at least a signal received from a sensor disposed within an area, a noise level experienced by a user in said area during a first time, said noise level being correlated with an ototoxic effect for said user;
determine, based on said ototoxic effect for said user, a threshold ototoxic noise level for said user;
determine, during a second time, based on one or more other signals received from the sensor, one or more other noise levels experienced by the user; and
in an instance in which at least one of the one or more other noise levels exceed the threshold ototoxic noise level, cause transmission of an alert or notification.

2. The apparatus of claim 1, wherein the ototoxicity application, when executed by the processor, further causes the processor to:
receive, from said sensor, the sensor signal identifying the noise level experienced by the user; and
correlate the noise level with the ototoxic effect for said user.

3. The apparatus of claim 2, wherein the signal is a first signal and the ototoxic effect is a first ototoxic effect, and wherein the ototoxicity application, when executed by the processor, further causes the processor to:
receive, from said sensor, a second signal identifying a second noise level experienced by the user during a third time in the area;
correlate the first noise level and the second noise level to a second ototoxic effect; and
adjust the threshold ototoxic noise level for the individual based on the second ototoxic effect.

4. The apparatus of claim 3, wherein the second ototoxic effect is determined based on an exposure, by the user, to a chemical comprising a pharmaceutical compound.

5. The apparatus of claim 1, wherein the ototoxicity application, when executed by the processor, further causes the processor to:
determine a personal protective equipment guideline based on the first noise level and the threshold ototoxic noise level; and
cause the personal protective equipment guideline to be sent to the individual.

6. The apparatus of claim 1, wherein the ototoxicity application, when executed by the processor, further causes the processor to:
receive the signal from a gas sensor disposed within the area; and
identify the first noise level in response to receiving the first signal from the gas sensor.

7. The apparatus of claim 1, wherein the ototoxicity application, when executed by the processor, further causes the processor to:
in response to receiving the first signal, receive a chemical exposure mapping of the area, wherein the chemical exposure mapping is determined from a plurality of sensor inputs within the area.

8. The apparatus of claim 7, wherein the ototoxicity application, when executed by the processor, further causes the processor to:
correlate the noise level experienced by the user in said area during said first time and said chemical exposure mapping of the area with the ototxic effect for the user.

9. The apparatus of claim 8, wherein the noise sensor detects the noise level at an ear of the user.

10. The apparatus of claim 1, wherein the first ototoxic effect is correlated with at least one of an exposure to a chemical in the environment, an exposure to a pharmaceutical composition, one or more environmental parameters, one or more physiological parameters, or a combination thereof.

11. A method comprising:
determining, based on at least a signal received from a sensor disposed within an area, a noise level experienced by a user in said area during a first time, said noise level being correlated with an ototoxic effect for said user;
determining, based on said ototoxic effect for said user, a threshold ototoxic noise level for said user;
determining, during a second time, based on one or more other signals received from the sensor, one or more other noise levels experienced by the user; and
in an instance in which at least one of the one or more other noise levels exceed the threshold ototoxic noise level, causing transmission of an alert or notification.

12. The method of claim 11, further comprising:
receiving, from said sensor, the sensor signal identifying the noise level experienced by the user; and
correlating the noise level with the ototoxic effect for said user.

13. The method of claim 12, wherein the signal is a first signal and the ototoxic effect is a first ototoxic effect, the method further comprising:
receiving, from said sensor, a second signal identifying a second noise level experienced by the user during a third time in the area;
correlating the first noise level and the second noise level to a second ototoxic effect; and
adjusting the threshold ototoxic noise level for the individual based on the second ototoxic effect.

14. The method of claim 13, wherein the second ototoxic effect is determined based on an exposure, by the user, to a chemical comprising a pharmaceutical compound.

15. The method of claim 11, further comprising:
determining a personal protective equipment guideline based on the first noise level and the threshold ototoxic noise level; and
causing the personal protective equipment guideline to be sent to the individual.

16. The method of claim 11, further comprising:
receiving the signal from a gas sensor disposed within the area; and
identifying the first noise level in response to receiving the first signal from the gas sensor.

17. The method of claim 11, further comprising:
in response to receiving the first signal, receiving a chemical exposure mapping of the area, wherein the chemical exposure mapping is determined from a plurality of sensor inputs within the area.

18. The method of claim 17, further comprising:
correlating the noise level experienced by the user in said area during said first time and said chemical exposure mapping of the area with the ototoxic effect for the user.

19. The method of claim 11, wherein the first ototoxic effect is correlated with at least one of an exposure to a chemical in the environment, an exposure to a pharmaceutical composition, one or more environmental parameters, one or more physiological parameters, or a combination thereof.

20. A computer program product comprising at least one computer-readable non-transitory memory medium having program code instructions stored thereon, the program code instructions, when executed by an apparatus comprising at least one processor, cause the apparatus to:
determine, based on at least a signal received from a sensor disposed within an area, a noise level experienced by a user in said area during a first time, said noise level being correlated with an ototoxic effect for said user;
determine, based on said ototoxic effect for said user, a threshold ototoxic noise level for said user;
determine, during a second time, based on one or more other signals received from the sensor, one or more other noise levels experienced by the user; and
in an instance in which at least one of the one or more other noise levels exceed the threshold ototoxic noise level, cause transmission of an alert or notification.

* * * * *